US00PP18713P2

(12) United States Plant Patent
Austin

(10) Patent No.: US PP18,713 P2
(45) Date of Patent: Apr. 8, 2008

(54) SHRUB ROSE PLANT NAMED 'AUSHOMER'

(50) Latin Name: *Rosa hybrida*
Varietal Denomination: AUShomer

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 11/635,856

(22) Filed: Dec. 8, 2006

(51) Int. Cl.
*A01H 5/00* (2006.01)

(52) U.S. Cl. ..... Plt./103

(58) Field of Classification Search ..... Plt./103
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

A new and distinct variety of shrub rose plant substantially as herein shown and described, characterized particularly by its creamy-white, cupped, double blooms; moderate, fruity fragrance with a hint of citrus; and its neat, compact, branches with few thorns.

1 Drawing Sheet

Genus and species: *Rosa hybrida.*
Variety denomination: 'AUShomer'.

ORIGIN OF THE INVENTION

The present invention relates to a new and distinct variety of a shrub rose plant named 'AUShomer' which was originated by me by crossing an unnamed, unpatented seedling with an unnamed, unpatented seedling.

BACKGROUND OF THE INVENTION

The primary objective of this breeding was to produce a free flowering, healthy variety with creamy-white blooms on a neat, compact shrub.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Creamy white, cupped, double blooms.
2. A neat, compact, branching shrub with few thorns.
3. A moderate fruity fragrance with a hint of citrus.

Asexual reproduction of this new variety by budding, as performed at Bowling Green Lane, Albrighton, England, shows that the foregoing and all other characteristics and distinctions come true to form and are established and transmitted through succeeding propagations.

Comparison with Parents

The seed parent has large, dark crimson blooms with a light, Old Rose fragrance. The pollen parent has pink, rosette-shaped blooms and rather rugose foliage.

Comparison with Similar Variety

'AUSquest' (U.S. Plant Pat. No. 14,092) has a greater petalage than 'AUShomer', and larger blooms which are more creamy-apricot in color. The leaves of 'AUSquest' are a darker shade of green and are slightly glossier than those of 'AUShomer'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants commencing at one year of age grown in a garden environment at Bowling Green Lane, Albrighton, England.

Blooming habit: Recurrent. The number of blooms per plant during the growing season is profuse; there are too many to count.

Bud:
*Size.*—About 3.5 cm long and 2.5 cm in diameter when the petals start to unfurl.
*Form.*—The bud form is pointed ovoid.

*Color.*—When sepals first divide, bud color is Yellow-Green Group 145C with patches of Red Group 51A. When half blown, the upper sides of the petals are Yellow Group 4C overlaid with Yellow-Orange Group 22C in base zone, and with irregular patches of Red Group 51C, and the lower sides of the petals are Yellow Group 4C top and middle zones, and Yellow Group 6D base zone.

*Sepals.*—Color: Upper surface: Yellow-Green Group 144A. Lower surface: Yellow-Green Group 144A with irregular patches of Red Group 46A. Length: 2.2 cm. Width: 1.0 cm. Shape: Subulate. Surface texture: Upper surface: Pubescent. Lower surface: Smooth. There are three lightly appendaged sepals. There are two unappendaged sepals with canescent edges.

*Receptacle.*—Color: Yellow-Green Group 144A. Shape: Campanulate. Size: Medium, about 1.5 cm long×0.9 cm wide. Surface: Smooth.

*Peduncle.*—Length: Medium, averaging about 7 cm. Surface: Glandular. Color: Yellow-Green Group 144A with a touch of Greyed-Purple Group 187A before the bud unfurls. Strength: Strong.

Bloom:

*Size.*—Medium. Average open diameter is about 7.5 cm.

*Borne.*—Several together in irregular, compound corymb clusters of six to seven blooms.

*Form.*—When first open: Cupped. Permanence: Retains its form to the end.

*Petalage.*—Number of petals under normal conditions: 80–85.

*Color.*—The upper sides of the petals are White Group 155B. The reverse sides of the petals are White Group 155B. The base of each petal is Yellow Group 8C.

*Discoloration.*—The general tonality at the end of the first day is White Group 155B, and at the end of the third day is White Group 155B.

*Fragrance.*—Moderate; fruit with hints of citrus.

Petals:

*Texture.*—Smooth.

*Size.*—Width: 2.8 cm. Length: 3.6 cm.

*Surface.*—Smooth.

*Shape.*—Inner petals: Obovate. Outer petals: Obdeltoid. Margin: Notched. Apex Shape: Some obtuse but most are cuspidate. Base Shape: Cuneate. Form: Incurved (tips of very outer petals slightly recurved).

*Arrangement.*—Imbricated.

*Petaloids.*—None.

*Persistence.*—Petals drop off cleanly before drying.

*Lastingness.*—On the plant: Fair (about 4 days). As a cut flower: Not tested.

Reproductive parts:

*Stamens.*—Number: 50–55. Length: 7–9 mm. Anthers: Length: 2 mm. Color: Yellow-Orange Group 17A. Arrangement: Regular around styles. Filaments: Color: Yellow Group 13C. Length: 5–7 mm. Pollen: Color: Yellow-Orange Group 17A.

*Pistils.*—Number: 30–35. Length: 9 mm. Styles: Color: Green-Yellow Group 1C. Length: 8 mm. Stigmas: Color: Yellow-Orange Group 18A. Length: 1 mm.

*Hips.*—None observed.

PLANT

*Form.*—Shrub.

*Growth.*—Vigorous, bushy.

*Age at maturity.*—Two years.

*Mature plant.*—Height: 1.25 m. Width: 0.75 m.

*Rootstock.*—'Dr Huey' in the USA. *Rosa dumetorum* 'Laxa' for the observed plants in the U.K.

Foliage: Number of leaflets on normal mid-stem leaves: 5 or 7 (including terminal leaflet).

*Size.*—Medium. About 16.4 cm long×12.6 cm wide.

*Quantity.*—Normal. Number of leaves per flowering stem: 8–10.

*Color.*—New foliage: Upper side: Yellow-Green Group 146B with Greyed-Purple Group 183B concentrated around margin. Lower side: Yellow-Green Group 146B overlaid heavily with Greyed-Purple Group 183C. Old foliage: Upper side: Green Group 137A. Lower side: Yellow-Green Group 146B.

Leaflets:

*Size.*—About 6.6 cm long×4.5 cm wide.

*Shape.*—Ovate.

*Base shape.*—Rounded.

*Apex shape.*—Cuspidate.

*Texture.*—Leathery, matt.

*Edge.*—Serrated.

*Serrations.*—Mainly single, some double; large.

*Petiole.*—Color: Yellow-Green Group N144D. Length: 3–4 cm. Width: 2 mm. Surface texture: Smooth, with prickles on underside.

*Petiole rachis.*—Color: Yellow-Green Group N144D. Underside: With prickles.

*Stipules.*—Length: 1.3–1.6 cm, serrated. Color: Yellow-Green Group 144B.

*Auricle.*—Shape: Subulate. Length: 5–6 mm. Width: 2 mm, tapering to a point. Color: Yellow-Green Group 144B.

*Disease resistance.*—Resistant to powdery and downy mildew, blackspot and rust in normal growing conditions.

*Pest resistance.*—Not tested.

*Vein color.*—Yellow-Green Group N144D.

*Venation pattern.*—Reticulate.

Wood:

*New wood.*—Color: Yellow-Green Group 144A overlaid with Greyed-Red Group 182A. Bark: Smooth.

*Old wood.*—Color: Yellow-Green Group 144A. Bark: Smooth.

Stems:

*Mature stem.*—Length: 30–50 cm. Diameter: 6 mm.

*Internode distance.*—6–8 cm. The above measurements are all variable, depending on growing conditions in a season.

Prickles:

*Quantity.*—On main canes from base: Few, 5 per 10 cm stem length. On laterals from main canes: Few, 1–2 per 10 cm per stem length.

*Form.*—Concave, curved inward.

*Length.*—5 mm.

*Color when young.*—Greyed-Red Group 179A.

*Color when mature.*—Greyed-Orange Group 175A.

Small prickles:

*Quantity.*—On main stalks: None. On laterals: None.

Winter hardiness: Not tested.

I claim:

1. A new and distinct variety of shrub rose plant substantially as herein shown and described, characterized particularly by its creamy-white, cupped, double blooms; moderate, fruity fragrance with a hint of citrus; and its neat, compact, growth with few thorns.

* * * * *

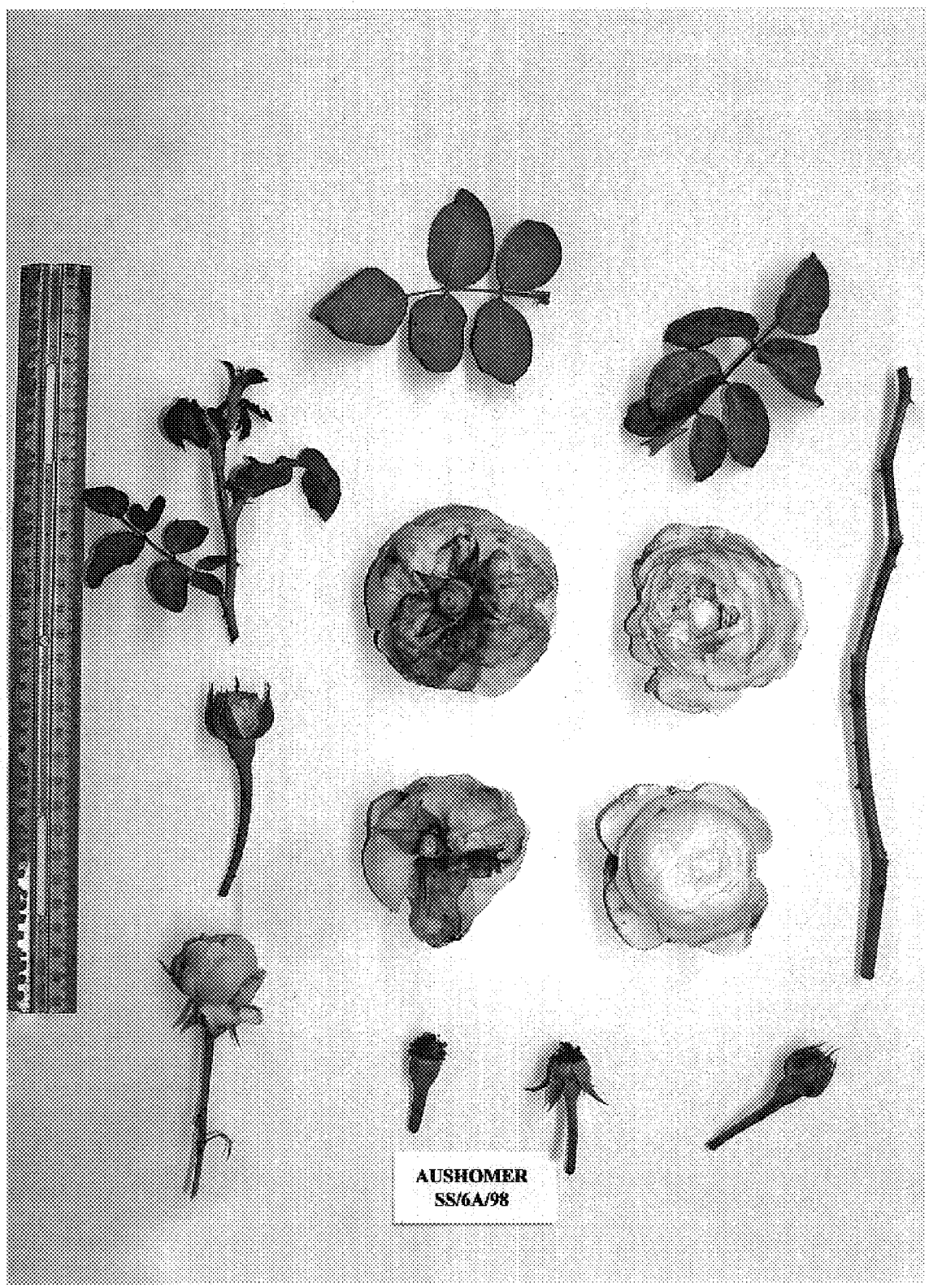
AUSHOMER
SS/6A/98